(12) United States Patent
Voet

(10) Patent No.: US 6,723,750 B2
(45) Date of Patent: Apr. 20, 2004

(54) PHOTODYNAMIC THERAPY FOR PRE-MELANOMAS

(75) Inventor: Martin A. Voet, San Juan Capistrano, CA (US)

(73) Assignee: Allergan, Inc., Irvine, CA (US)

( * ) Notice: Subject to any disclaimer, the term of this patent is extended or adjusted under 35 U.S.C. 154(b) by 43 days.

(21) Appl. No.: 10/099,239

(22) Filed: Mar. 15, 2002

(65) Prior Publication Data

US 2003/0176411 A1 Sep. 18, 2003

(51) Int. Cl.$^7$ ............................................. A61K 31/19
(52) U.S. Cl. ...................... 514/568; 514/185; 514/545; 514/576; 514/578
(58) Field of Search ................................ 514/545, 568, 514/576, 578, 185

(56) References Cited

U.S. PATENT DOCUMENTS

| | | |
|---|---|---|
| 3,592,930 A | 7/1971 | Katz et al. |
| 3,989,815 A | 11/1976 | Rajadhyaksha |
| 3,989,816 A | 11/1976 | Rajadhyaksha |
| 3,991,203 A | 11/1976 | Rajadhyaksha |
| 4,017,615 A | 4/1977 | Shastri et al. |
| 4,411,893 A | 10/1983 | Johnson et al. |
| 4,906,457 A | 3/1990 | Ryan |
| 4,935,498 A | 6/1990 | Sessler et al. |
| 5,162,509 A | 11/1992 | Sessler et al. |
| 5,179,120 A | 1/1993 | Vogel et al. |
| 5,252,720 A | 10/1993 | Sessler et al. |
| 5,256,399 A | 10/1993 | Sessler et al. |
| 5,272,142 A | 12/1993 | Sessler et al. |
| 5,292,414 A | 3/1994 | Sessler et al. |
| 5,369,101 A | 11/1994 | Sessler et al. |
| 5,439,570 A | 8/1995 | Sessler et al. |
| 5,451,576 A | 9/1995 | Sessler et al. |
| 5,457,183 A | 10/1995 | Sessler et al. |
| 5,475,104 A | 12/1995 | Sessler et al. |
| 5,504,205 A | 4/1996 | Sessler et al. |
| 5,525,325 A | 6/1996 | Sessler et al. |
| 5,559,207 A | 9/1996 | Sessler et al. |
| 5,565,552 A | 10/1996 | Magda et al. |
| 5,567,687 A | 10/1996 | Magda et al. |
| 5,569,759 A | 10/1996 | Sessler et al. |
| 5,576,013 A | 11/1996 | Williams |
| 5,580,543 A | 12/1996 | Sessler et al. |
| 5,583,220 A | 12/1996 | Sessler et al. |
| 5,587,371 A | 12/1996 | Sessler et al. |
| 5,587,463 A | 12/1996 | Sessler et al. |
| 5,591,422 A | 1/1997 | Hemmi et al. |
| 5,594,136 A | 1/1997 | Sessler et al. |
| 5,595,726 A | 1/1997 | Magda et al. |
| 5,599,923 A | 2/1997 | Sessler et al. |
| 5,599,928 A | 2/1997 | Hemmi et al. |
| 5,601,802 A | 2/1997 | Hemmi et al. |
| 5,607,924 A | 3/1997 | Magda et al. |
| 5,622,946 A | 4/1997 | Sessler et al. |
| 5,714,328 A | 2/1998 | Magda et al. |
| 5,776,925 A | 7/1998 | Young et al. |
| 5,798,491 A | 8/1998 | Magda et al. |
| 5,913,884 A | 6/1999 | Trauner et al. |
| 6,022,526 A | 2/2000 | Woodburn et al. |
| 6,034,267 A * | 3/2000 | Gierskcky et al. .......... 560/155 |
| 6,043,237 A | 3/2000 | Meadows et al. |
| 6,114,321 A | 9/2000 | Platzek et al. |
| 6,136,841 A | 10/2000 | Platzek et al. |
| 6,187,030 B1 | 2/2001 | Gart et al. |
| 6,225,333 B1 | 5/2001 | Rodgers et al. |
| 6,297,228 B1 | 10/2001 | Clark |

FOREIGN PATENT DOCUMENTS

| | | |
|---|---|---|
| DE | 2411382 A1 | 9/1975 |
| EP | 0316179 B1 | 1/1994 |
| GB | 2058077 A | 4/1981 |
| GB | 2360461 A | 9/2001 |
| WO | WO 90/10633 | 9/1990 |
| WO | WO 94/29316 | 12/1994 |
| WO | WO 95/10307 | 4/1995 |
| WO | WO 95/21845 | 8/1995 |
| WO | WO 95/24930 | 9/1995 |
| WO | WO 96/09315 | 3/1996 |
| WO | WO 96/38461 | 12/1996 |
| WO | WO 96/40253 | 12/1996 |

OTHER PUBLICATIONS

Goldman, L., et al., "Preliminary investigative studies with PDT in dermatologic and plastic surgery," Lasers in Surgery and Medicine 5:453–456 (1985).

Kurwa, H.A., et al., "The role of photodynamic therapy in dermatology," Clinical and Experimental Dermatology, 1999 Blackwell Science Ltd, 24, pp. 143–148.

Szeimies, R–M, et al., "Topical photodynamic therapy in dermatology," Journal of Photochemistry and Photobiology B: Biology 36 (1996) pp. 213–219.

Varma, S., et al., Bowen's disease, solar keratoses and superficial basal cell carcinomas treated by photodynamic therapy using a large–field incoherent light source, British Journal of Dermatology 2001: 144: pp. 567–574.

Wolf, P., et al., Topical photodynamic therapy with endogenous porphyrins after application of 5–aminolevulinic acid Journal of the American Academy of Dermatology, 1993;28:17–21.

Batlle, A.M., *Porphyrins, Porphyrias, cancer and photodynamci therapy—a model for carcinogenesis*, J. Photochem. Photobiol. B: Biol., 20 (1993) 5–22.

Beems, E.M., et al., *Photosensitizing Properties of Bacteriochlorophyllin a and Bacteriochlorina, Two Derivatives of Bacteriochlorophyll a*, Photochemistry and Photobiology, vol. 46, No. 5, pp. 639–643 1987.

(List continued on next page.)

*Primary Examiner*—Dwayne C. Jones
(74) *Attorney, Agent, or Firm*—Stephen Donovan

(57) ABSTRACT

Method for treating dermal pre-melanoma conditions which include administering an effective amount of a photosensitive agent to a dermal pre-melanoma cell and activating the photosensitive agent, thereby treating a dermal pre-melanoma condition.

19 Claims, No Drawings

OTHER PUBLICATIONS

Brown, J.E., et al., *Photodynamic Therapy–13 New Light On Cancer Treatment*, JSDC vol. 115, Sep. 1999, pp. 249–153.

Bryson, C., *Tracking the sequence from suntan to skin cancer*, University of Alberta Express News, www.expressnews.ualberta.ca/expressnews/articles/news.cfm?p_ID–599, 2 pgs., Nov. 9, 2001.

Gurinovich, G.P., *Photodynamic activity of chlorin $e_6$ and chlorin $e_6$ ethylenediamide in vitro and in vivo*, J. Photochem. Photobiol. B: Biol., 13 (1992) 51–57.

Karrer, S., et al., *Role of Lasers and Photodynamic Therapy in the Treatment of Cutaneous Malignancy*, AM J. Clin Dermatol 2001:2(4) pp. 229–237.

Kessel, D. *Interactons between porphyrins and mitochondrial benzodiazepine receptors*, Cancer Letters, 39 (1988) 193–198.

Kessel, D. *Determinants of photosensitization by purpurins*, Photochemistry and Photobiology vol. 50, No. 2, pp. 169–174, 1989.

Kessel, D, et al., *Photosensitization with Derivatives of Chlorophyll*, Photochemistry and Photobiology, vol. 49, No. 2, pp. 157–160, 1989.

Kreimer–Birnbaum, M., *Modified porphyrins, chlorins, phthalocyanines, and purpurins: Second–generation phtosensitizers for photodynamic therapy*, Seminars in Hematology, vol. 26, No. 2 (Apr.) 1989: pp 157–173.

Morgan, A.R., et al., *Metallopurpurins and light: effect on transplantable rate bladder tumors and murine skin*, Photochemistry and Photobiology, vol. 51, No. 5, pp. 589–592, 1990.

Newell, J., *The Lamp that Kills Cancer Cells Like a Low Cost Laser*, Britannia Internet Magazine, www.britannia.com/science/laser.html, 3 pgs., Nov. 9, 2001.

Stoughton, R. et al., *Azone: A new non–toxin Enhancer of Cutaneous Penetration*, Drug Development and Industrial Pharmacy, 9(4), pp. 725–744, (1983).

Tonnesen, P. et al., *A double–blind trial of a 16–hour transdermal nicotine patch in smoking cessation*, The New England Journal of Medicine, Aug. 1, 1991, vol. 325, No. 5, pp. 311–315.

VanDenBergh, H., *Light and porphyrins in cancer therapy*, Chemistry in Britain, May 1986, pp. 430–439.

Woodford, R., et al., *Penetration Enhancers and the Percutaneous Absorption of Drugs: an Update*, J. Toxicol. Cut. & Ocular Toxicol. 5(3), 167–177 (1986).

Author unknown, *Actinic Keratoses Treatment, Decision Memorandum*, www.hcfa.gov/coverage/8b3–t4.htm, 18 pgs. Nov. 9, 2001.

Author unknown, *Treatment of Premalignant Lesions*, www.indiacancer.org/cali/preles.html, 4 pgs, Nov. 9, 2001.

Author unknown, *Photodynamic Therapy (PDT) The CancerBACUP factsheet*, www.cancerbacup.org.uk/info/pdt.htm, 3 pgs, Nov. 9, 2001.

Author unknown, *Cancer Cream*, www3.utsouthwestern.edu/library/consumer/cancreme.htm, 2 pgs., Nov. 9, 2001.

Author unknown, *What are the types of Melanoma*, www.advocatehealth.com/healthinfo/articles/cancercare/me14.html, 2 pgs, Jan. 21, 2002.

* cited by examiner

PHOTODYNAMIC THERAPY FOR PRE-MELANOMAS

BACKGROUND

The present invention relates to methods for treating pre-melanomas. In particular the present invention relates to methods for treating a pre-melanoma cell or condition using a photosensitive agent.

Photodynamic Therapy

Photodynamic therapy (PDT) is the use of an agent, given orally, intravenously, or topically, that can be activated or energized by light to inactivate or to cause necrosis of a target tissue in which the agent has accumulated. Activation of the agent results in the formation of new molecules and free radicals that form other chemicals that, in turn, can destroy the target tissue to varying extents or otherwise have a deleterious effect on the target tissue. Thus, photodynamic therapy involves the application of a photosensitive (photochemotherapeutic) agent to an affected area of the body, followed by exposure of the photosensitive agent to light of a suitable wavelength to activate the photosensitive agent and convert it into a cytotoxic form, whereby the affected cells are killed or their proliferative potential is diminished.

A photosensitive agent can exert its desired effects by a variety of mechanisms, directly or indirectly. Thus for example, a photosensitizer can become directly toxic when activated by light, whereas other photosensitive agents act to generate toxic species, for example, oxidizing agents such as singlet oxygen or other oxygen-derived free radicals, which are extremely destructive to cellular material and biomolecules such as lipids, proteins and nucleic acids.

PDT is not effective to treat thick lesions such as the skin cancer melanoma. Hence, PDT is not used to treat melanoma. Karrer, S., et al., *Role of Lasers and photodynamic therapy in the treatment of cutaneous malignancy*, Am J Clin Dermatol 2001;2(4):229–37. See also Brown J. E., et al., *Photodynamic therapy—new light on cancer treatment*, JSDC 115;249–253:1999.

Photodynamic therapy has been used to treat various superficial (i.e. thin, exterior, surface lesions) abnormalities or disorders of the skin as well as to treat macular degeneration. Thus, PDT has been used to treat various cancerous lesions, such as basal cell carcinoma including certain non-malignant lesions, and superficial skin lesions such as actinic keratoses ("AKs") and psoriasis.

The PDT topical agent 5-aminolevulinic acid (5-ALA) has been used to selectively photosensitize the atypical cells of an AK lesion. Approximately 14 to 18 hours following application of the 5-ALA, the skin is exposed to a light source and the cells of the AK lesion are destroyed. Common side effects of PDT include erythema, stinging/burning, edema, and scaling or crusting of the lesion. The primary disadvantage of PDT to treat AK is the need for treatment over a 2-day period.

Precancerous Skin Lesions

Perhaps the most common precancerous skin lesion is actinic keratose (AK), also known as solar keratoses, which are common, sun-induced precancerous skin lesions that are confined to the epidermis. AK typically appears as circumscribed, rough, scaly patches on sun exposed skin, ranging from flesh-colored to reddish brown. Due to their distinctive roughened quality, AKs are easy to detect by palpation or by visualization. AKs are usually 1 to 3 mm in diameter, but may be larger in size and may appear in clusters. AKs are dynamic in nature. Although most AKs are asymptomatic, some may exhibit signs and symptoms such as thickening, burning, tenderness, or itching. AKs may also progress to squamous cell carcinoma (SCC), a form of skin cancer. AKs are most prevalent in fair-skinned individuals with a history of significant sun exposure. The prevalence of AKs increases with advancing age, and AKs are more common in men than women. AKs are more common in immunosuppressed patients and in patients with some genetic disorders (such as xeroderma pigmentosum). Due to high rates of prevalence and incidence, destruction of AKs is the most commonly performed outpatient dermatologic procedure in the United States.

The current management options for visible or easily perceived and diagnosed precancerous dermatological lesions such as AKs include cryosurgery with liquid nitrogen, topical treatments, and curettage. Other less common treatments include dermabrasion, excision, chemical peels, laser therapy, and photodynamic therapy.

Topical treatments, such as the chemotherapeutic agent 5-fluorouracil (5-FU), are most commonly used for patients with multiple lesions. The 5-FU cream is applied to the entire region that is affected, and the recommended course of treatment involves several applications per day over a 2 to 4 week time span. 5-FU selectively targets the damaged skin, causing an inflammatory response with erythema, necrosis, and erosion. Numerous side effects are associated with 5-FU, including pain or irritation, tenderness, ulceration, burning, and inflammation. As a result, patient compliance is a significant concern with this treatment.

Curettage, which involves the use of a curette to scrape away the lesion, is another common method of treatment for easily perceptible precancerous skin lesions. In some instances, curettage may be used in combination with electrosurgery to stop bleeding or apply more damage to the affected area. The primary advantage of curettage is the ability to submit the specimen for histologic analysis, particularly in cases where invasive squamous cell carcinoma is suspected. Disadvantages of curettage include the need for local anesthesia and the potential for scarring.

Melanoma and Pre-Melanoma

Melanoma is a type of potentially fatal skin cancer. A melanoma tumor develops from abnormal melanocytes in the lower epidermis. A melanocyte is a pigment cell which can become abnormal to varying degrees. The highest degree of abnormality of a melanocyte cell is to become a melanoma cell. A melanoma cell is a malignancy (i.e. a cancer or tumor cell) that invades and destroy surrounding tissues and can metastasize to distant sites in the body via the blood and lymph systems.

Melanomas are graded according to the deepest depth to which they penetrate the skin tissue. The depth may be described in terms of millimeters (Breslow) or by the depth level of various structures in the skin tissue to which the melanoma has penetrated. Melanoma is curable in its earliest phases and can arise on its own or from an atypical or unusual mole. More than 90% of melanomas occur on the visible portions of the body, that is on the skin.

The incidence and mortality rates of malignant melanoma continue to rise dramatically throughout the world. In the United States, it is estimated that nearly one in 90 Americans will develop melanoma. Melanoma is one of the most feared neoplasms because of the high mortality associated with metastasis. Melanomas usually metastasize first via the lymphatic system, with involvement of regional nodes, and then via blood vessels, with dissemination to subcutaneous tissue and to the liver, lungs, and brain. The presence of regional lymph node metastasis is predictive of a poor prognosis.

As set forth, melanomas arise from melanocytes and are typically pigmented (melanotic) due to accumulation of melanin, which imparts a dark color to melanomas. Some melanocytes may be less well differentiated and therefore produce little or no melanin. Melanomas arising from melanocytes can be nonpigmented or amelanotic.

Approximately 70 percent of melanomas are of the superficial spreading type. Generally, this type of melanoma is characterized by a pre-existing mole that slowly changes over a period of one to five years which is then followed by a period of rapid changes close to the time that the melanoma is diagnosed. Typically, this type of melanoma first appears as a very dark area in an existing mole. As the pre-melanoma enlarges, the edges usually appear notched or indented. Superficial spreading melanoma may appear anytime after puberty and is seen more often in women than in men.

Nodular melanoma is the second most common type of melanoma, accounting for approximately 15 to 30 percent of cases. These melanomas usually do not appear in an existing nevi. Instead, they start as melanomas and are often darker in color than the superficial spreading type. Nodular melanomas typically take on a blue-black appearance and look like blood blisters. Some may have shades of purple, gray or red in them, or lack color and have a fleshy appearance. They are usually 1 cm to 2 cm or larger in diameter. Nodular melanomas appear more often in men and are usually seen in middle age, although they may appear at any age.

A small percentage of melanomas, 4 to 10 percent, are lentigo maligna melanomas. They differ greatly from other types in that they usually do not metastasize. They are seen most often on the face and neck, are typically large (greater than 3 cm) and are tan-colored with shades of brown. They appear most often in Caucasian women who are over the age of 50.

Acral lentiginous melanomas generally occur on the palms of the hand or the soles of the feet. They may also be seen under a fingernail or toenail. Their incidence is low in Caucasians (only 2 to 8 percent of those having melanoma), but substantially higher among darker-skinned individuals with melanoma (approximately 35 to 60 percent). They appear on average over a two-and one-half-year period and resemble a flat tan or brown stain. It is common for this type of melanoma to break into a sore. Acral lentiginous melanoma is usually seen in persons who are over the age of 60. Physicians currently use CT scans, radionuclide bone scans, liver and spleen scintigraphy, and magnetic resonance imaging to evaluate the extent of melanoma. Usually these tests are conducted when specific symptoms require investigation. However, a biopsy is currently the only recognized definitive means of identifying the melanoma.

Melanoma usually occurs in adults, but it may occasionally be found in children and adolescents. Men most often get melanoma on the trunk (the area of the body between the shoulders and hips) or on the head or neck, and women most often get melanoma on the arms and legs. In rare cases, it can develop in parts of the body not covered by the skin, such as the eyes, mouth, large intestine, or vagina.

Melanoma can be difficult to cure, and is often lethal. In the U.S. there are about 38,000 new cases of melanoma a year and approximately 7,000 melanoma deaths occur every year in the U.S. Current therapy for melanoma has many deficiencies and drawbacks. The first line therapy of choice is to remove the melanoma tissue as well as a substantial area of tissue surrounding the melanoma so as to also remove precancerous, premelanoma cells which typically exist in proximity to the melanoma. Premelanoma cells are those melanocytes in proximity to a melanoma, such as, for example, a lentigo maligna melanoma, which while not malignant, are irregular and/or atypical melanocytes which if left untreated often become malignant over time. Surgical removal of the melanoma and surrounding tissue results in scaring and the removal of a large areas of tissue can necessitate use of skin grafts. Additionally, where a facial melanoma is removed a highly undesirable cosmetic outcome can result due to the scaring and discoloration of the new skin graft.

Early treatment of melanoma is highly desirable for patient prognosis and there is a need for an effective treatment of melanoma while it is still a pre-melanoma condition. Additionally, there is a need for an effective treatment of pre-melanoma cells in the vicinity of excised melanoma tissue. Thus it is very preferable to treat melanoma in the pre-melanoma stage. Treatment of melanoma at the pre-melanoma stage may greatly increase the prognosis for a patient. Therefore, what is needed are effective methods to treat pre-melanoma. While it is known to treat certain cancerous tissues with PDT and to treat discernable and superficial precancerous tissues (such as AKs) by PDT, there exists no PDT therapy for precancerous pre-melanoma tissues. Note that pre-melanoma cannot be discerned visually or by a tactile examination.

SUMMARY

The present invention meets this need and provides for new methods to treat pre-melanoma which involve photo-dynamic therapy. A pre-melanoma is a precancerous cell or cells that, if left untreated, can develop into a melanoma (cancer) cell. Thus, a pre-melanoma includes pre-superficial spreading melanoma, pre-lentigo melanoma, pre-nodular melanoma and pre-acral lentiginous melanoma. A pre-melanoma cell can be identified, for example, histologically as an atypical or irregular melanocyte.

In accordance with the present invention there are provided methods for treating a pre-melanoma, such as a dermal pre-melanoma, condition and/or for preventing development of a melanoma. By "dermal" it is meant the skin which comprises the epidermis, dermis and adjacent subcutaneous tissue. These methods may include administering an effective amount of a photosensitive agent to a pre-melanoma cell and activating the photosensitive agent. In one embodiment, the photosensitive agent is a porphyrin, for example, a porphyrin having formula I:

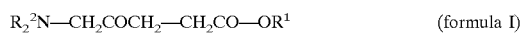

$$R_2^2N\text{—}CH_2COCH_2\text{—}CH_2CO\text{—}OR^1 \quad \text{(formula I)}$$

wherein $R^1$ is alkyl or substituted alkyl; and each $R^2$ is independently hydrogen, alkyl or substituted alkyl. An alkyl $R^1$ and/or an alkyl $R^2$ may be substituted with a group selected from the group consisting of hydroxyl, alkoxy, acyloxy, alkoxycarbonyloxy, amino, aryl, oxo and fluoro. In addition, $R^1$ and/or $R^2$ may be interrupted by an atom selected from the group consisting of oxygen, nitrogen, sulfur and phosphorus. Salts of these compositions and mixtures and combinations of the compositions are also contemplated for use in accordance with the present invention.

In accordance with the present invention, the dermal pre-melanoma cell may be, for example, a pre-superficial spreading melanoma cell, a pre-lentigo melanoma cell, a pre-nodular melanoma cell or a pre-acral lentiginous melanoma cell.

In one embodiment of the present invention, the administering includes applying the photosensitive agent to the dermal pre-melanoma cell. The administering may also include waiting for a time period wherein the photosensitive agent reaches an effective concentration in the dermal pre-melanoma cell.

After administration, the photosensitive agent may be activated. The photosensitive agent may be activated by irradiating the dermal pre-melanoma cell with light for an effective length of time and/or an effective wavelength to activate the photosensitive agent.

In one embodiment the dermal pre-melanoma condition is treated by causing necrosis or apoptosis of a dermal pre-melanoma cell and/or by causing a melanoma cell to become a non-melanoma cell. In one embodiment of the present invention a dermal pre-melanoma cell is located at a site near where a melanoma was removed. For example, a dermal pre-melanoma may be within about 0.1 cm of the site from where the melanoma was removed or within about 2 cm of the site from where the melanoma was removed or within about 5 cm of the site from where the melanoma was removed or within about 20 cm or more of the site from where the melanoma was removed.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DESCRIPTION

The present invention is based upon the discovery that a photosensitive agent can be used to treat a pre-melanoma. A pre-melanoma is a cell or cells that if left untreated can develop into melanoma, for example, superficial spreading melanoma, lentigo melanoma, nodular melanoma and acral lentiginous melanoma. There is no effective current therapy for pre-melanoma except excision. Examples of pre-melanoma are pre-superficial spreading melanoma, pre-lentigo melanoma, pre-nodular melanoma and pre-acral lentiginous melanoma. It is surprising that PDT can be used effectively with regard to a pre-melanoma because the histological nature and biochemical function of a pre-melanoma cell is distinct from that of a cancerous cell and from other precancerous cells such as AK cells. Thus, it was unexpected that a pre-melanoma cell would selectively absorb sufficient photosensitive agent to permit effective treatment by the methods disclosed herein. Additionally, since PDT is ineffective to treat melanoma, it is surprising that PDT can be used to treat pre-melanoma, the precursor of melanoma.

A photosensitizer is a chemical compound which produces a biological effect, for example, a cytotoxic effect, upon photoactivation. A photosensitizer used in accordance with the present invention has a sufficiently low toxicity to permit administration to the patient with a medically acceptable level of safety. In one embodiment, the photosensitizer is essentially nontoxic, except for the desired cytotoxic effect produced locally, upon activation of the photosensitizer.

A single photosensitizer compound can be used alone in the practice of this invention. Alternatively, two or more photosensitizers can be used in a mixture or in a combination or both. The mechanism of the biological effect produced upon photoactivation need not be of a particular type, as long as the desired treatment of pre-melanoma is achieved. The mechanism of the cytotoxic effect may depend upon the particular photosensitizer used. The cytotoxic effect may result from, for example, the generation of a short-lived, highly reactive, diffusible species such as singlet oxygen or free radicals. Singlet oxygen or free radicals may then react with double bonds and initiate free radical chain reactions which may inactivate biologically active molecules such as growth factors or cytokines. Such a reaction process may also degrade or disorganize biological membranes of cells that participate directly or indirectly in forming a pre-melanoma.

The photosensitizer can be chosen, or chemically modified, to optimize its usefulness in specific treatment situations. For example, the photosensitizer may be chemically conjugated to a targeting moiety such as a monoclonal antibody for targeting to a particular tissue. Administration of the photosensitizer may be local or systemic. The administration may be by any suitable route, including topical, intravenous, intraarticular, subcutaneous, intramuscular, intraventricular, intracapsular, intraspinal, intraperitoneal, intranasal, oral, buccal, rectal or vaginal. The preferred route of administration will depend on the size and nature of the pre-melanoma, and on the location of the pre-melanoma.

A photosensitizer agent (or synonymously a photosensitive agent or PDT agent) can be administered to the intended area of target tissue, which target tissue then absorbing and accumulates the agent. In general, healthy tissues eliminate photosensitizer agents used in photodynamic therapy relatively rapidly while the agent is retained in target cell areas for longer periods of time.

Medical practitioners and researchers in the field understand that the optimum time for activation can vary between different photosensitizer compounds, as different compounds can have different bioabsorption rates, stabilities, and elimination rates, and the time can vary as a function of the treatment location in the body, and so forth, as will be appreciated by persons of skill in the field. Predetermined guidelines and protocol for the timing of the irradiation step will often be available in advance for a given photosensitizer agent and specific treatment, or they can be determined empirically for any given set of conditions.

Pre-melanoma is typically found in the skin (i.e. dermal pre-melanoma). However, pre-melanoma may also occur in the eye and is called ocular pre-melanoma or intraocular pre-melanoma. Pre-melanoma may also arise in the meninges, the digestive tract, lymph nodes, or areas where melanocytes are found.

The size, nature, and location of the pre-melanoma being treated may render local administration of the photosensitizer feasible. Local administration may reduce the likelihood of unwanted side effects. In addition, local administration may permit greater control over photosensitizer concentration at the pre-melanoma site.

In the preferred embodiment of the present invention, a photosensitizer is locally administered to a dermal location in close proximity to where a melanoma was removed. For example, after surgically removing a melanoma, a photosensitizer may be applied to an area including and/or surrounding the site of excision. The area of application around the site of excision may be as large or as small as deemed necessary by a treating physician, but is chosen so as to treat pre-melanoma cells which can circumscribe the excised melanoma For example, the area of application may be between about 0.1 cm$^2$ and 1.0 cm$^2$, or between about 0.1 cm$^2$ and about 10 cm$^2$ or between about 0.1 cm$^2$ and about 100 cm$^2$ or between about 0.1 cm$^2$ and about 2000 cm$^2$.

In another embodiment of the present invention, a photosensitizer is locally administered to a site at and/or near a pre-melanoma, that is an atypical or irregular melanocyte. For example, a photosensitizer may be applied to an area including and/or surrounding a pre-melanoma. The area of application may be as large or as small as deemed necessary by a treating physician. For example, the area of application may be between about 0.1 cm$^2$ and 1.0 cm$^2$, or between about 0.1 cm$^2$ and about 10 cm$^2$ or between about 0.1 cm$^2$ and about 100 cm$^2$ or between about 0.1 cm$^2$ and about 2000 cm$^2$.

To facilitate sufficient absorption of the photosensitive agent by pre-melanoma cells in the lower epidermis various chemical transport enhancers (such as the skin lipid fluidizer Azone), and diverse methodologies, such as ionotophoresis, can be used, to thereby enhance percutaneous penetration of the agent to a pre-melanoma cell. For example, decylmethyl sulfoxide ("DMS") is known to increase permeation of the skin. Additionally, ethanol pretreatment of the skin in conjunction with iontophoresis can also be used to facilitate penetration of the selected PDT agent to the lower epidermis. A variety of organic solvents as well as surfactants can also be used for this purpose. Furthermore, use of an adhesive patch for transdermal delivery of a therapeutic drug is known. See e.g. Tonnesen, P. et al., *A double blind trial of a 16-hour transdermal nicotine patch in smoking cessation*, New Eng J Medicine, 325(5); 311–315: August 1991. The present invention encompasses an adhesive patch (as a PDT agent depot) placed onto the surface of the skin of the patient, where the patch comprises a polymeric carrier which can release a therapeutically effective amount of a PDT agent onto the skin surface of the patient. Application of a PDT agent adhesive, polymeric patch can be preceded by pretreatment of the skin with i.e. ethanol wipes or dermal abrasion, and the patch can be used concurrently or in conjunction with a suitable permeation enhancement methodology such as iontophoresis.

Separately or in conjunction with use of a substance or process to enhance penetration of and accumulation of the PDT agent to pre-melanoma cells, the light source used to activate the PDT agent is selected so as to permit activation of the agent in the lower epidermis. Thus, the light source can comprise a penetrating form of radiation, such as UV radiation or laser light with a focus in the lower epidermis, and/or the irradiation of the target area can be maintained for a time period such that a therapeutically effective amount of the PDT agent accumulated in pre-melanoma cells in the lower epidermis is activated.

Photosensitizers

Various photosensitizers are known and may be used in the practice of this invention. Photosensitizers typically have chemical structures that include multiple conjugated rings that allow for light absorption and photoactivation. They may differ in the properties of light absorption and fluorescence, biodistribution, temporal uptake, and mechanisms of photoactivatable cytotoxicity.

Classes of photosensitizers include hematoporphyrins (Batlle, J. Photochem. Photobiol. B-Biol. 20:5–22 (1993); Kessel, Cancer Let. 39:193–198 (1988)), uroporphyrins, phthalocyanines (Kreimer-Birnbaum, Seminars in Hematology 26:157–173 (1989)), purpurins (Morgan et al., Photochem. Photobiol. 51:589–592 (1990); Kessel, Photochem. Photobiol. 50:169–174 (1989)), acridine dyes, bacteriochlorophylls (Beems et al., Photochem. Photobiol. 46:639–643 (1987); Kessel et al., Photochem. Photobiol. 49:157–160 (1989)), and bacteriochlorins (Gurinovich et al., J. Photochem. Photobiol. B-Biol. 13:51–57 (1992)), porphyrins, bacteriochlorins, naphthalocyanines, texaphyrines, and non-tetrapyrrole photosensitizers.

Some specific examples of suitable photosensitizers which can be used in the practice of the present invention are listed in Table 1.

TABLE 1

1. Photofrin®
2. synthetic diporphyrins and dichlorins
3. hydroporphyrins, e.g., chlorins and bacteriochlorins of the tetra(hydroxyphenyl) porphyrin series
4. O-substituted tetraphenyl porphyrins (picket fence porphyrins)
5. 3,1-meso tetrakis (o-propionamido phenyl) porphyrin
6. verdins
7. purpurins, e.g., tin and zinc derivatives of octaethylpurpurin (NT2), and etiopurpurin (ET2)
8. chlorins, e.g., chlorin e6, and mono-l-aspartyl derivative of chlorin e6
9. benzoporphyrin derivatives (BPD), e.g., benzoporphyrin monoacid derivatives, tetracyanoethylene adducts of benzoporphyrin, dimethyl acetylenedicarboxylate adducts of benzoporphyrin, Diels-Adler adducts, and monoacid ring "a" derivative of benzoporphyrin
10. low density lipoprotein mediated localization parameters similar to those observed with hematoporphyrin derivative (HPD)
11. sulfonated aluminum phthalocyanine (Pc) sulfonated AlPc disulfonated (AlPcS.sub.2) tetrasulfonated derivative sulfonated aluminum naphthalocyanines chloroaluminum sulfonated phthalocyanine (CASP)
12. zinc naphthalocyanines
13. anthracenediones
14. anthrapyrazoles
15. aminoanthraquinone
16. phenoxazine dyes
17. phenothiazine derivatives
18. chalcogenapyrylium dyes cationic selena and tellurapyrylium derivatives
19. ring-substituted cationic PC
20. pheophorbide®
21. texaphyrins
22. protoporphyrin
23. tin etiopurpurin
24. methylene blue
25. 5-amino levulinic acid
26. esters of 5-amino levulinic acid Texaphyrins are aromatic pentadentate macrocyclic "expanded porphyrins" useful in photodynamic therapy. Texaphyrin is considered as being an aromatic benzannulene containing both 18p- and 22p-electron delocalization pathways. Texaphyrin molecules absorb strongly in the tissue-transparent 700–900 nm range, and they exhibit inherent selective uptake or biolocalization in certain target tissues. Texaphyrins have exhibited significant tumor selectivity as detected by fluorescence and magnetic resonance imaging. Texaphyrins and water-soluble texaphyrins, method of preparation and various uses have been described in U.S. Pat. Nos. 5,798,491, 4,935,498; 5,162,509; 5,252,720; 5,256,399; 5,272,142; 5,292,414; 5,369,101; 5,432,171; 5,439,570; 5,451,576; 5,457,183; 5,475,104 5,504,205;

5,525,325; 5,559,207; 5,565,552; 5,567,687; 5,569,759; 5,580,543; 5,583,220; 5,587,371; 5,587,463; 5,591,422; 5,594,136; 5,595,726; 5,599,923; 5,599,928; 5,601,802; 5,607,924; and 5,622,946; PCT publications WO 90/10633, 94/29316, 95/10307, 95/21845, 96/09315, 96/38461 and 96/40253; allowed U.S. patent application Ser. Nos. 08/484, 551, 08/591,318 and 08/624,311; and pending U.S. patent application Ser. Nos. 08/657,947, 08/700,277 and 08/763, 451; each patent, publication, and application is incorporated in its entirety herein by reference.

The present invention also provides for use of esters of 5-aminolevulinic acids or pharmaceutically acceptable salts thereof to treat pre-melanoma. These photosensitizers are described in U.S. Pat. No. 6,034,267 which is incorporated in its entirety herein by reference.

In esters of 5-aminolevulinic acids, the 5-amino group may be substituted or unsubstituted.

More particularly, the 5-aminolevulinic acids may be esters with optionally substituted alkanols, for example, alkyl esters or substituted alkyl esters. Database Xfire, entries 3060978, 5347132, 5499790, 5620924, 5633390, 5991317 and 6517740 (Beilstein); Cosmo Sogo Kenkyusho KK, Patent Abstracts of Japan, Vol 16; No. 156 (C-0930), 16.4.1992; EP-A-316179 (Tokuyama Soda KK); GB-A-2058077 (Hudson et al) and DE-A-2411382 (Boehringer Sohn Ingelheim) describe alkyl ester derivative of 5-aminolevulinic acid, and derivatives and salts thereof and processes for their preparation.

The invention may therefore be seen to provide for the use of compounds of formula I

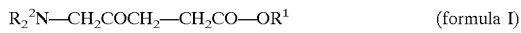
$$R_2^2N\text{—}CH_2COCH_2\text{—}CH_2CO\text{—}OR^1 \qquad \text{(formula I)}$$

salts thereof and mixtures thereof, wherein $R^1$ and $R^2$ may represent an alkyl optionally substituted by hydroxy, alkoxy, acyloxy, alkoxycarbonyloxy, amino, aryl, oxo or fluoro groups and optionally interrupted by oxygen, nitrogen, sulfur or phosphorus atoms and $R^2$ may represent a hydrogen atom. Each $R^2$ may be the same or different.

The substituted alkyl groups may be mono or polysubstituted. Thus, suitable groups include, for example, unsubstituted alkyl, alkoxyalkyl, hydroxyalkoxyalkyl, polyhydroxyalkyl, hydroxy poly alkyleneoxyalkyl and the like. The term "acyl" as used herein includes both carboxylate and carbonate groups, thus, acyloxy substituted alkyl groups include for example alkylcarbonyloxy alkyl. In such groups any alkylene moieties may have carbon atom contents defined for alkyl groups below. Certain aryl groups include phenyl and monocyclic 5–7 membered heteroaromatics, especially phenyl and such groups may themselves optionally be substituted. Representative substituted alkyl groups include alkoxymethyl, alkoxyethyl and alkoxypropyl groups or acyloxymethyl, acyloxyethyl and acyloxypropyl groups, for example, pivaloyloxymethyl.

Certain compounds for use according to the invention, include those wherein $R^1$ represents an unsubstituted alkyl group and/or each $R^2$ represents a hydrogen atom.

As used herein, the term "alkyl" includes any long or short chain, straight-chained or branched aliphatic saturated or unsaturated hydrocarbon group. The unsaturated alkyl groups may be mono- or polyunsaturated and include both alkenyl and alkynyl groups. Such groups may contain 1 to about 40 carbon atoms. Alkyl groups containing 1 to about 10 are commonly used. For example, 8, 6 or 4 carbon atoms may be used.

In certain embodiments, ALA-methylester, ALA-ethylester, ALA-propylester, ALA-hexylester, ALA-heptylester and ALA-octylester and salts thereof, represent certain compounds for use according to the invention. The compounds for use according to the present invention may take the form of pharmaceutically acceptable salts. Such salts may be acid addition salts with physiologically acceptable organic or inorganic acids. Suitable acids include, for example, hydrochloric, hydrobromic, sulfuric, phosphoric, acetic, lactic, citric, tartaric, succinic, maleic, fumaric and ascorbic acids. Procedures for salt formation are conventional and are well known in the art.

The esters of 5-aminolevulinic acid may exert their effects by enhancing production of Protoporphyrin IX (Pp); upon delivery to the desired site of action hydrolytic enzymes such as esterases present in the target cells break down the esters into the parent ALA, which then enters the haem synthesis pathway and leads to a build-up of Pp. The ester compounds may have advantages over ALAs. First, the compounds may better be able to penetrate skin and other tissues as compared with ALA; the penetration is both deeper and faster. This is an important advantage, especially for topical administration. Second, the esters have may be better enhancers of Pp production than ALA; Pp production levels following administration of the ALA esters are higher than with ALA alone. Third, the compounds may have improved selectivity for the target tissue to be treated, namely the Pp production-enhancing effect may be localized to the pre-melanoma and not spread to the surrounding tissues. Finally, the compounds may localize better to the pre-melanoma upon administration. This means that undesirable photosensitization effects may be reduced or avoided. The present invention provides for the use of the herein described compounds, or a pharmaceutically acceptable salt thereof, for use in the treatment and or detection of pre-melanoma.

The internal and external body surfaces which may be treated according to the invention include the skin and all other epithelial and serosal surfaces, including and any other area of the body where a pre-melanoma may exist.

Formulations

The compositions of the invention can be formulated in conventional manner with one or more physiologically acceptable carriers or excipients, according to techniques well known in the art. Compositions may be administered topically, orally or systemically. Topical compositions may be particularly useful in accordance with the present invention, and include gels, creams, ointments, sprays, lotions, salves, sticks, soaps, powders, pessaries, aerosols, drops and any of the other conventional pharmaceutical forms known in the art.

Photosensitizing agents can be more effective for photodynamic therapy when used as part of a formulated composition. For example, the agents may have better adhesion characteristics, may remain more stable in storage and through transportation, may be less susceptible to bacterial contamination, and may be readily applied.

Suitable formulations contain a sufficient amount of light photosensitive agent to be effective with photodynamic therapy. For example, see U.S. Pat. No. 5,179,120 which is incorporated in its entirety herein by reference.

Methods well known in the art for making formulations may be found in, for example, "Remington's Pharmaceutical Sciences." Formulations may contain, for example, as excipients sterile water or saline, Cremophor EL, polyalkylene glycols such as polyethylene glycol, oils of vegetable origin, or hydrogenated naphthalenes biocompatible, biodegradable lactide polymer, or polyoxyethylene-polyoxypropylene copolymers. Other potentially useful formulation components may include ethylene-vinyl acetate copolymer particles, osmotic pumps, implantable infusion systems, liposomes, and antibody conjugates.

Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

Formulations for parenteral administration may also include glycocholate for buccal administration, methoxysalicylate for rectal administration, or citric acid for vaginal administration.

Topical formulations may be prepared in gel form by combining the photophotosensitive agent with a solvent and adding a gelling agent thereto. Suitable gelling agents include carboxymethyl cellulose (Carbopol.TM. 934P from B. F. Goodrich of Brecksville, Ohio U.S.A.) and fumed silica (CAB-O-SIL®, Cabot Corp., Tuscola, Ill.). The gelling agent is generally used in amounts of about 5–10 wt % to obtain a gel with the desired viscosity. Obviously, gels containing more or less gelling agent will have slightly higher or lower viscosity. One skilled in the art may readily obtain the desired gel viscosity by adjusting the concentration of gelling agent.

Additives, such as cosolvents, surfactants and/or bioadhesives frequently improve the formulation properties and may be added as desired. Suitable cosolvents/surfactants include propylene glycol and glycerine. Suitable bioadhesives include carboxymethylcellulose, polyacrylic polymers, chitosan and sodium alginate, modified starch with polyacrylic polymers, eudispert hv hydrogels or xerogels, sodium hyaluronate, and polymers of polyethylene glycol, hydroxypropylcellulose, or carboxyvinyl. The additives may be incorporated into the formulation by mechanically mixing the additives into the mixture. Other additives may be used to enhance or maintain chemical stability and physiological suitability. Examples are antioxidants, chelating agents, inert gases, buffers and isotonicifiers.

Examples of antioxidants and typical concentration ranges include acetone sodium bisulfite (about 0.1% to about 2%), ascorbic acid (about 0.05% to about 5%), monothioglycerol (about 0.1% to about 10%), potassium metabisulfite (about 0.05% to about 1%), propyl gallate (about 0.02%), sodium bisulfite (about 0.01% to about 1.0%), sodium formaldehyde sulfoxylate (about 0.03% to about 1%), sodium metabisulfite (about 0.02% to about 1%), sodium sulfite (about 0.01% to about 1%), sodium thioglycolate (about 0.05% to about 1%).

Chelating agents may beneficially be included in order to enhance accumulation of Pp; the chelation of iron by the chelating agents may prevent incorporation of iron into Pp to form haem by the action of the enzyme ferrochelatase, thereby leading to a build-up of Pp. The photosensitizing effect is thus enhanced.

Examples of chelating/complexing agents and example concentration ranges include edetate sodium (about 0.005% to about 2%), edetate calcium disodium (about 0.005% to about 0.01%), gentisic acid ethanolamide (about 1.0% to about 2.0%), niacinamide (about 1.0% to about 5%), sodium citrate (about 0.01% to about 5%), citric acid (about 0.001% to about 1.0%). However, a chelating agent may conveniently be used at a concentration of about 0.1% to about 40% (w/w), for example, about 2% to about 10% (w/w). Aminopolycarboxylic acid chelating agents are useful in the present invention. These include any of the chelants described in the literature for metal detoxification or for the chelation of paramagnetic metal ions in magnetic resonance imaging contrast agents. Particular mention may be made of EDTA, CDTA (cyclohexane diamine tetraacetic acid), DTPA and DOTA. To achieve the iron-chelating effect, desferrioxamine and other siderophores may also be used, for example, in conjunction with aminopolycarboxylic acid chelating agents such as EDTA.

Buffers may be used to stabilize a formulation. Buffer systems employed normally have as low a buffer capacity as feasible in order to not disturb significantly the body buffer systems if injected.

The buffer range and effect of the buffer on activity may be evaluated. Appropriate adjustment may be useful to provide the optimum conditions for pH dependent partition into the target malignant tissues or pre-melanoma area. Examples of such buffer systems include the following acids: acetic, adipic, ascorbic, benzoic, citric, glycine, lactic, tartaric, hydrochloric, phosphoric, sulfuric, carbonic and bicarbonic; and their corresponding salts such as: potassium, sodium, magnesium, calcium and diethanolamine salts. A surface-penetration assisting agent may be any of the skin-penetration assisting agents described in the pharmaceutical literature e.g. HPE-101 (available from Hisamitsu), DMSO and other dialkylsulphoxides, in particular n-decylmethylsulphoxide (NDMS), dimethylsulphacetamide, dimethylformamide (DMFA), dimethylacetamide, glycols, various pyrrolidone derivatives (Woodford et al., J. Toxicol. Cut. & Ocular Toxicology, 1986, 5: 167–177), and Azone® (Stoughton et al., Drug Dpv. Ind. Pharm. 1983, 9: 725–744.

DMSO has a number of beneficial effects. Thus, in addition to the surface-penetration assisting effect (DMSO is particularly effective in enhancing the depth of penetration of the active agent into the tissue), DMSO has anti-histamine and anti-inflammatory activities. In addition, DMSO has been found to increase the activity of the enzymes ALA-synthase and ALA-dehydrogenase (the enzymes which, respectively, form and condense ALA to porphobilinogen) thereby enhancing the formation of the active form, Pp.

The surface penetration agent may conveniently be provided in a concentration range of about 2% to about 50% (w/w), for example, about 10% (w/w).

Some other surface penetration agents are proparacaine, dimethyl sulfoxide, dimethyl acetamide, dimethylformamide, 1-methyl-2-pyrrolidone, diisopropyladipate, diethyltoluamide and to a lesser extent propylene glycol. Additional penetration agents include substituted azacycloalkan-2-ones having from 5 to 7 carbons in the cycloalkyl group such as 1-dodecylazacycloheptan-2-one (AZONE) and other azacycloalkan-2-ones such as described in U.S. Pat. No. 3,989,816 incorporated herein in its entirety by reference. Also included are N-bis-azocyclopentan-2-onyl alkanes described in U.S. Pat. No. 3,989,815 (incorporated herein by reference), 1-substituted azacyclopentan-2-ones described in U.S. Pat. No. 3,991,203 (incorporated herein by reference) and water-soluble tertiary amine oxides described in U.S. Pat. No. 4,411,893 (incorporated herein by reference).

The topical formulations contain a sufficient amount of the photosensitizing compound to be effective in photodynamic therapy. Generally, concentrations in the range of about 0.001% to about 70%, for example, from about 1% to about 20%, may be used.

The photosensitizing agents may be used with solvents and adjuvants which are appropriate to the photosensitive agent chemistry to adjust the viscosity of the formulation. Some solvents that may be used for this purpose are ethanol, polyethylene glycols of the liquid series and propylene glycol. Also included are acetone, dimethyl acetamide, dimethyl formamide, dimethyl sulfoxide ethanol, glycerin, polyethylene glycol 300, and 400, propylene glycol, sorbitol, polyoxyethylene sorbitan fatty acid esters such as laureate, palmitate, stearate, and oleate, polyoxyethylated vegetable oil, sorbitan monopalmitate, 2-pyrrolidone; n-methyl-2-pyrrolidine; n-ethyl-1-pyrrolidine; tetrahydrofurfuryl alcohol, tween 80 and dimethyl isosorbide. Dimethyl isosorbide (ARLASOLVE® DMI, ICI Specialty Chemicals) has the advantage of being both water- and oil-soluble. Additionally, dimethyl isosorbide may be readily gelled with a gelling agent or mixed with lotion, cream or ointment to produce formulations with, for example, about 4% KLUCEL® (Hercules).

Additional topical formulations which may be used for chosen photosensitive agents are disclosed in U.S. Pat. Nos. 3,592,930 and 4,017,615 which are incorporated herein by reference. In certain formulations, the photosensitive agent is applied in an aqueous gel, lotion, cream or ointment formulation suitable for use on sensitive tissues. Such formulations may contain one or more bioadhesive polymers. The formulation may have a viscosity within the range from about 26,000 to about 1,500,000 cps at 20° C. and a pH and/or isosmotic make-up compatible with body tissues.

The compositions may also be provided in a form adapted for, for example, oral administration, parenteral administration, administration by injection, for example, by intradermal, subcutaneous, intraperitoneal or intravenous injection. Alternative pharmaceutical forms thus include plain or coated tablets, capsules, suspensions and solutions containing the active component optionally together with one or more inert conventional carriers and/or diluents, for example, with corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof.

The concentration of the compounds as described herein in the compositions, depends upon the nature of the compound, the composition, mode of administration and the patient and may be varied or adjusted according to choice. Generally however, concentration ranges of about 1% to about 90% (w/w) may be suitable, for example, about 10% to about 30% (w/w).

According to the condition being treated, and the nature of the composition, the compounds for use in the invention may be co-administered with the herein described formulation agents, for example, in a single composition, or they may be administered sequentially or separately. In many cases a particularly beneficial photochemotherapeutic effect may be obtained by pre-treatment with a surface-penetration assisting agent in a separate step, prior to administration of the compounds for use in the invention. Furthermore, in some situations a pre-treatment with the surface-penetration assisting agent, followed by administration of the photochemotherapeutic agent in conjunction with the surface-penetration assisting agent may be beneficial. When a surface-penetration assisting agent is used in pre-treatment, it may be used at a low to high concentration, for example, from about 0.1% to about 100% (w/w).

Methods of Use

A topical photosensitive agent may be applied to tissues that may contain a pre-melanoma one time or more, for example, 1 to 50 times or more a day for 1 to 20 days or more.

Following administration to the surface, the area treated may be exposed to light to achieve the photochemotherapeutic effect. In certain embodiments of the invention, the methods include a waiting step before the step of activating the photosensitizer. The waiting step is designed to allow the photosensitizer to reach an optimal tissue concentration at the pre-melanoma site, prior to photoactivation. If a waiting step is used, the length of the waiting step will depend on factors such as the route by which the photosensitizer is administered, the location of the pre-melanoma, and the speed with which the photosensitizer moves in the body. The waiting step may be, for example, about 1 second to about 0.5 h or about 0.5 h to about 1 h or about 1 h to about 24 h or about 1 day to about 50 days.

Light may be used to activate the photosensitizer. The size of the light coverage and duration of the exposure may be adjusted depending on the dimensions and location of the pre-melanoma. The specific size and duration of exposure may depend on the strength of the laser being used, the diameter of the pre-melanoma and the presence or absence of pigmentation. Methods for irradiation of different areas of the body by, for example, lamps or lasers are well known in the art (see, for example, Van den Bergh, Chemistry in Britain, May 1986 p. 430–439).

After application of the photosensitizer to a pre-melanoma the pre-melanoma site may be exposed to light of an effective wavelength and effective intensity, for an effective length of time. What wavelength, or range of wavelengths, is effective may depend on the photosensitizer (s) used. Wavelength specificity for photoactivation may depend on the molecular structure of the photosensitizer Delivery of the light used to photoactivate the photosensitizer may be limited to the pre-melanoma site or the pre-melanoma site plus an area surrounding the pre-melanoma site. This may minimize undesirable cytotoxic side effects.

The light for photoactivation may be produced and delivered to the pre-melanoma site by any suitable means. Some photosensitizer compounds may be activated by near infra-red and longer wavelength visible light. This allows deeper tissue penetration of the photoactivating light, thereby facilitating transillumination. Transillumination may be performed using a variety of devices. The devices may utilize laser or non-laser sources, for example, lightboxes or convergent light beams.

The irradiation will in general be applied at a dose level of about 1 to about 500 Joules/cm$^2$, for example at about 100 Joules/cm$^2$. A higher or lower dose level can be used as determined by a treating physician.

The applied energy level may also be adjusted by the number of times the energy is applied. The specific number of such energy applications will depend on the pre-melanoma. Some pre-melanomas may require 200 energy applications to reach an effective therapy, others only 1–50 energy applications, while others may need 3–4 sessions of 100 energy applications each. The number of energy applications used may be determined by a treating physician.

A laser energy delivered to the pre-melanoma per light burst in the present invention may be within the range from about 1 Joule/cm$^2$ (J/cm$^2$) to about 9000 J/cm$^2$, for example, within the range from about 1–900 J/cm$^2$, for example, within the range from about 5 J/cm$^2$ to about 500 J/cm$^2$. Typical treatments may involve anywhere from 1 to 4000 applications of laser energy to a pre-melanoma.

An aspect of the invention provides a method of photochemotherapeutic treatment of pre-melanoma of external or internal surfaces of the body, comprising administering to the affected surfaces, a composition as hereinbefore defined, and exposing said surfaces to light, for example, to light in the wavelength region 300–800 nm, for example 500–700 nm. The wavelength of light used for irradiation may be selected to achieve a more efficacious photochemotherapeutic effect. In one embodiment, when porphyrins are used in photochemotherapy they are irradiated with light at about the absorption maximum of the porphyrin. For example, use of ALA in photochemotherapy, wavelengths in the range of about 350 to about 640 nm, for example, about 610 to about 635 nm may be employed. However, by selecting a broad range of wavelengths for irradiation, extending beyond the absorption maximum of the porphyrin, the photosensitizing effect may be enhanced. Not wishing to be bound by any theory or mechanism of operation, this is thought to be due to the fact that when Pp, and other porphyrins, are exposed to light having wavelengths within its absorption spectrum, Pp is degraded into various photo-products included in particular photoprotoporphyrin (PPp). PPp is a chlorin and has a considerable photo-sensitizing effect; its absorption spectrum stretches out to longer wavelengths beyond the wavelengths at which Pp absorbs, for example, up to about 700 nm (Pp absorbs almost no light above 650 nm). Irradiation with wavelengths of light in the range 500–700 nm may be particularly effective. It may be particularly important to include the wavelengths 630 and 690 nm.

Light Sources

Light in a plurality of bursts from a laser may be applied to one or more pre-melanomas. On outer cutaneous, ocular, and buccal surfaces, the energy may be applied directly. Internal surfaces may require appropriate speculum retraction or endoscopic delivery. Fiber optic lasers may be used to deliver the energy with a high degree of precision.

Conventional monochromatic light sources may be used in the present invention by matching the wavelength of the emitted light to the sensitizing wavelength of the photosensitizing agents. Examples include monochromatic light from traditional Argon lasers, tunable dye lasers, pulsed metal vapor lasers (e.g., gold vapor, copper vapor pumped dye lasers, Nd:YAG pumped dye lasers), and solid-state lasers. The traditional argon laser is recognized as a standard, readily available laser used in virtually all clinics and hospitals.

The invention having been fully described, examples illustrating its practice are set forth below. These examples should not, however, be considered to limit the scope of the invention, which is defined by the appended claims.

EXAMPLES

Example 1

Treatment of Pre-Melanoma Subsequent to Abdominal Melanoma Removal

A 64 year old white male presents a mole on his abdomen that is approximately 2 cm across and has uneven borders. A shave biopsy is performed. Pathological analysis reveals a superficial spreading melanoma.

The melanoma is surgically removed and a photosensitive agent, for example, a porphyrin is applied to the site of the excision and to an area surrounding the excision of about 10 cm in diameter. The photosensitizer is included in a lotion at a concentration of about 10% to about 20% (w/w). The area of application is covered by a semi-permeable membrane dressing for approximately a 4 hour period after which time the dressing is removed and the application is repeated. After another 4 hour period the dressing is removed and the area is exposed to light in the wavelength range of about 500 nm to about 700 nm, for example, about 630 nm to about 690 nm for approximately 6 hours. After a 24 hour period, this process is repeated. Two years after treatment the patient is cancer free.

Example 2

Treatment of Pre-Melanoma Subsequent to Forearm Melanoma Removal

A 47-year-old woman seeks medical attention after noticing a tan colored mole with shades of brown located on her left forearm. Physical examination reveals the presence of an asymmetric shaped mole approximately 4 cm in diameter. The physician asks the patient about her family medical history and discovers that the patient's mother suffers from a rare form of non-malignant melanoma, maligna melanoma, since the age of 52. The doctor examines the rest of the patient's body for other moles and checks for swelling of the lymph nodes. No other suspect moles are found and the patient's nodes do not appear to be swollen.

A fine needle asperation (FNA) biopsy is performed on the mole. Pathological examination of the biopsied tissue reveals the presence of maligna melanoma.

The patient undergoes surgery for the removal of the melanoma. Following surgery the patient is treated for pre-melanoma using photodynamic therapy. An oil-in-water lotion which includes a porphyrin photosensitive agent at 20% (w/w), for example, a porphyrin comprising esters of 5-aminolevulinic acids at 20% (w/w) is applied to the area around the point of excision of the melanoma. The lotion is applied in a radius of about 8 cm of the site of excision of the melanoma. The area of application is covered by a semi-permeable membrane dressing for approximately a 24 hour period after which time the dressing is removed. The area is then exposed to light in the wavelength range of about 500 to about 700 nm for approximately 2 hours.

Three years after treatment the patient is cancer free.

Example 3

Treatment of Pre-Melanoma Subsequent to Melanoma Removal from Thigh

Upon noticing enlargement and apparent swelling of a mole on the left thigh, a 34 year old woman seeks medical attention. Physical examination reveals a large mole, approximately 2.5 cm across, that bleeds and is painful in response to touch. A positive diagnosis for superficial spreading melanoma is made based on microscopic examination of a skin biopsy sample.

The melanoma is surgically removed and the patient is treated for pre-melanoma using photodynamic therapy. The area around the point of excision of the melanoma is contacted with a composition which includes aminolevulinic acid methyl ester at about a 10% (w/w) and a penetrating agent, DMSO, at a concentration of about 10% (w/w). The composition is applied directly to and around the site of excision of the melanoma covering an area of approximately 100 cm$^2$. The application is repeated once an hour for an 8 hour period. The area is then exposed to light in the wavelength range of about 500 to about 700 nm for approximately 10 hours.

At one year after the treatment the patient presents no sign of cancer.

Example 4

Treatment of Pre-Melanoma Subsequent to Facial Melanoma Removal

A 38 year old man seeks medical attention after discovering a blue black colored mole that bleeds located on his forehead. Physical examination reveals the presence of an asymmetric shaped mole approximately 0.5 cm in diameter. The doctor examines the rest of the patient's body for other moles and checks for swelling of the lymph nodes. No other suspect moles are found and the patient's nodes do not appear to be swollen.

A fine needle asperation (FNA) biopsy is performed on the mole. Pathological examination of the biopsied tissue reveals the presence of maligna melanoma.

The patient undergoes surgery for the removal of the melanoma.

Following surgery the patient is treated for pre-melanoma using photodynamic therapy. A lotion which includes a photosensitive agent at 15% (w/w) is applied to the area around the point of excision of the melanoma. The lotion is applied in a radius of about 10 cm of the site of excision of the melanoma. The area of application is covered by a semi-permeable membrane dressing for approximately a 24 hour period after which time the dressing is removed and the application is repeated. This application process is repeated 3 more times. After the last application a period of 48 hours is allowed to pass. The area is then exposed to light in the wavelength range of about 500 to about 700 nm for approximately 2 hours.

At two years after treatment the patient is cancer free.

Example 5

Treatment of Pre-Melanoma Subsequent to Neck Melanoma Removal

A woman, age 55, upon examination reveals a mole on her neck that bleeds and is tender to touch. A positive diagnosis for nodular melanoma is made based on pathological examination of a tissue biopsy sample.

The melanoma is surgically removed and the patient is treated for pre-melanoma using photodynamic therapy. The area around the point of excision of the melanoma is contacted with a gel which includes esters of 5-amino levulinic acids at about 20% (w/w) and a penetrating agent, DMSO, at a concentration of about 10% (w/w). The gel is applied directly to and around the site of excision of the melanoma. The application is repeated every 2 hours for a 12 hour period. The area is then exposed to light in the wavelength range of about 500 to about 700 nm for approximately 6 hours.

At one week after treatment, several necrotic areas appear in the area of skin exposed to the photosensitizer and light source that are about 1 mm in diameter. These areas are diagnosed as pre-melanoma.

Five years after the treatment the patient is cancer free.

Example 6

Treatment of Pre-Melanoma Subsequent to Foot Melanoma Removal

A 36 year female seeks a physical medical exam after discovering an irregular shaped mole that has a "hard and lumpy feel" on the sole of her left foot. The treating physician performs a punch biopsy. Pathological examination reveals acral lentiginous melanoma localized to the dermis portion of the skin.

The melanoma is surgically removed and the patient is treated for pre-melanoma using photodynamic therapy. The area around the point of excision of the melanoma is contacted with an ointment which includes amino levulinic acid methyl ester at about 5% (w/w) and a penetrating agent, DMSO, at a concentration of about 15% (w/w). The ointment is applied directly to and around the site of excision of the melanoma. The site of application is covered with a semi-permeable membrane for 24 hours after which the application is repeated and again covered for a 24 hour period. The area is then exposed to light in the wavelength range of about 610 nm to about 670 nm for approximately 2 hours once a day for four straight days. The patient is checked monthly for the spread of cancer for the first 6 months after surgery and every two months thereafter. Two years after surgery there is no sign of the cancer.

I claim:

1. A method for treating a pre-melanoma cell, the method comprising the steps of:
    a) administering an effective amount of a photosensitive agent to a pre-melanoma cell and
    b) activating the photosensitive agent, thereby treating a pre-melanoma cell.

2. The method of claim 1 wherein the administering step includes topical application of the photosensitive agent to a dermal pre-melanoma cell.

3. The method of claim 2 wherein the administering step includes waiting for a time period wherein the photosensitive agent reaches an effective concentration in the dermal pre-melanoma cell.

4. The method of claim 1 wherein the photosensitive agent is activated by irradiating the pre-melanoma cell with light of an suitable wavelength for an effective length of time, thereby activating the photosensitive agent.

5. The method of claim 1 wherein the pre-melanoma cell is treated by causing necrosis or apoptosis of the dermal pre-melanoma cell.

6. The method of claim 1 wherein the pre-melanoma cell is selected from the group consisting of a pre-lentigo melanoma cell, a pre-nodular melanoma cell, pre-maligna melanoma cell and a pre-acral lentiginous melanoma cell.

7. The method of claim 1 wherein the photosensitive agent comprises a porphyrin.

8. The method of claim 1 wherein the photosensitive agent is selected from the group consisting of compounds having formula I, salts thereof and mixtures thereof, wherein formula I is:

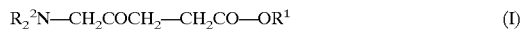

$$R_2^2N\text{---}CH_2COCH_2\text{---}CH_2CO\text{---}OR^1 \quad (I)$$

wherein $R^1$ is alkyl or substituted alkyl; and each $R^2$ is independently hydrogen, alkyl or substituted alkyl.

9. The method of claim 8 wherein the alkyl $R^1$ and/or the alkyl $R^2$ are substituted with a group selected from the group consisting of hydroxyl, alkoxy, acyloxy, alkoxycarbonyloxy, amino, aryl, oxo and fluoro.

10. The method of claim 8 wherein $R^1$ and/or $R^2$ are interrupted by an atom selected from the group consisting of oxygen, nitrogen, sulfur and phosphorus.

11. The method of claim 1 wherein the pre-melanoma cell is located at a site within about 10 cm of a site of a melanoma removal.

12. A method for treating a dermal pre-melanoma cell, the method comprising the steps of:
    a) administering an effective amount of a photosensitive agent to a dermal pre-melanoma cell at a site in proximity to a prior melanoma excision and
    b) activating the photosensitive agent thereby treating a dermal pre-melanoma cell.

13. A method for treating a dermal pre-melanoma cell, the method comprising the steps of:
    a) administering an effective amount of a photosensitive agent selected from the group consisting of compounds having formula I, salts thereof and mixtures thereof, wherein formula I is:

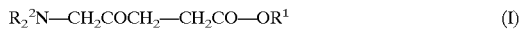
$$R_2{}^2N\text{—}CH_2COCH_2\text{—}CH_2CO\text{—}OR^1 \qquad (I)$$

wherein $R^1$ is alkyl or substituted alkyl; and each $R^2$ is independently hydrogen, alkyl or substituted alkyl to a dermal pre-melanoma cell and b) activating the compound thereby treating a dermal pre-melanoma cell.

14. The method of claim 13 wherein the alkyl $R^1$ and/or the alkyl $R^2$ are substituted with a group selected from the group consisting of hydroxyl, alkoxy, acyloxy, alkoxycarbonyloxy, amino, aryl, oxo and fluoro.

15. The method of claim 13 wherein $R^1$ and/or $R^2$ are interrupted by an atom selected from the group consisting of oxygen, nitrogen, sulfur and phosphorus.

16. The method of claim 13 wherein the administering includes applying the photosensitizer to the dermal pre-melanoma cell.

17. The method of claim 16 wherein the administering includes waiting for a time period wherein the formula I composition reaches an effective concentration in the dermal pre-melanoma cell.

18. The method of claim 13 wherein the compound is activated by irradiating the dermal pre-melanoma cell with light for an effective length of time which activates the photosensitive agent.

19. A method for treating a dermal pre-melanoma cell, the method comprising the steps of:

a) administering an effective amount of a photosensitive agent selected from the group consisting of compounds having formula I, salts thereof and mixtures thereof, wherein formula I is:

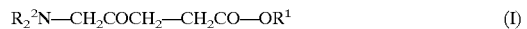
$$R_2{}^2N\text{—}CH_2COCH_2\text{—}CH_2CO\text{—}OR^1 \qquad (I)$$

wherein $R^1$ is alkyl or substituted alkyl; and each $R^2$ is independently hydrogen, alkyl or substituted alkyl to a site in proximity to a melanoma excision site and b) activating the formula I thereby treating a dermal pre-melanoma cell.

* * * * *